US008602128B2

(12) United States Patent
Ligneul et al.

(10) Patent No.: US 8,602,128 B2
(45) Date of Patent: Dec. 10, 2013

(54) ANALYSIS OF DRILLING CUTTINGS FOR PERMITTIVITY

(75) Inventors: Patrice Ligneul, Chaville (FR); Valerie Judith Anderson, Cambridge (GB); Tianhua Zhang, Al-Khobar (SA); Gerald Henry Meeten, Ware (GB); Andrew Clarke, Cambridge (GB); Mohammed Badri, Al-Khobar (SA)

(73) Assignee: Schlumberger Technology Corporation, Sugar Land, TX (US)

( * ) Notice: Subject to any disclaimer, the term of this patent is extended or adjusted under 35 U.S.C. 154(b) by 376 days.

(21) Appl. No.: 13/097,393

(22) Filed: Apr. 29, 2011

(65) Prior Publication Data
US 2012/0273273 A1 Nov. 1, 2012

(51) Int. Cl.
*E21B 21/01* (2006.01)
*E21B 21/06* (2006.01)

(52) U.S. Cl.
CPC ..................................... *E21B 21/06* (2013.01)
USPC ............................ 175/206; 175/207; 175/46

(58) Field of Classification Search
USPC .......................................... 175/207, 206, 46
See application file for complete search history.

(56) References Cited

U.S. PATENT DOCUMENTS

| | | | |
|---|---|---|---|
| 4,185,238 A * | 1/1980 | Huchital et al. | ............... 324/338 |
| 4,899,112 A | 2/1990 | Clark et al. | |
| 4,979,393 A | 12/1990 | Leung et al. | |

OTHER PUBLICATIONS

International Search Report and Written Opinion of PCT Application No. PCT/US2012/035418 dated Sep. 12, 2012: pp. 1-10.
Egermann et al., "SPE 77563: A Fast and Direct Method of Permeability Measurements on Drill Cuttings," SPE Reservoir Evaluation & Engineering, Aug. 2005: pp. 269-725.
Førdedal et al., "Crude oil emulsions in high electric fields as studied by dielectric spectroscopy. Influence of interaction between commercial and indigenous surfactants," Colloids and Surfaces A: Physicochemical and Engineering Aspects, 1996, vol. 106: pp. 33-47.
Knight et al., "A new concept in modeling the dielectric response of sandstones: Defining a wetted rock and bulk water system," Geophysics, May 1990, vol. 55(5): pp. 586-594.
Leung et al., "IADC/SPE 23887: Dielectric Constant Measurements: A New, Rapid Method to Characterize Shale at the Wellsite," IADC/SPE Drilling Conference, 1992: pp. 401-408.
Marsala et al., "SPE/ISRM 47202: Transient method implemented under Unsteady-State conditions for Low and very Low Permeability measurements on Cuttings," SPE International, 1998: pp. 33-39.
Saasen et al., "IADC/SPE 112687: Automatic Measurement of Drilling Fluid and Dril Cuttings Properties," SPE International, 2008: pp. 1-17.
Santarelli et al., "Formation Evaluation fro Logging on Cuttings," SPE Reservoir Evaluation & Engineering, Jun. 1998: pp. 238-244.
Syunyaev et al., "Effects of Temperature and Pressure on the Phase State of Oils and Asphaltene Solutions Observed Using Dieletric Spectroscopy," Energy Fuels, 2010, vol. 24(4): pp. 2233-2239.

* cited by examiner

*Primary Examiner* — Cathleen Hutchins
(74) *Attorney, Agent, or Firm* — Bridget Laffey; Rachel E. Greene; Jakub M. Michna

(57) ABSTRACT

Systems and methods for analysis of drilling cuttings are described. Complex permittivity is measured of rock cutting samples obtained during drilling operations. The origin of the cuttings is known by flow rate analysis in the drilling system. Various means can be used for rock cutting dielectric measurement. For example, the dielectric measurement can be made by matching the unknown permittivity of the medium to be analyzed to the permittivity of known liquid mixtures by successive saturation and looking for a "zero-contrast" measurement.

17 Claims, 3 Drawing Sheets

ANALYSIS OF DRILLING CUTTINGS FOR PERMITTIVITY

FIELD

This patent specification generally relates to analysis of drilling cuttings. More particularly, this patent specification relates to the use of analysis techniques for determining permittivity of drilling cuttings.

BACKGROUND

Among the reservoir characterization technologies devoted to oilfields, complex permittivity measurements can provide information on the water saturation and the cementation factor of the rock formation in the vicinity of the borehole. Complex permittivity can be obtained from measurements made using wire line tools. For example, see tools such as The Schlumberger Electromagnetic Propagation Tool or The Schlumberger Dielectric Scanner tool working at various frequencies. There are three main features in rock systems that are important for understanding the broadband dielectric response: the rock solid polarization, fluid polarization, and rock-fluids interaction in the polarization process. In addition, in certain circumstances the fluid-fluid interfacial polarization can provide further information.

Tools such as Schlumberger's Dielectric Scanner tool measures the characteristics of propagation of travelling electromagnetic waves between emitting and receiving antennae. The dielectric permittivity and the conductivity of the geological formation at various frequencies are deduced from these data by inversion methods. From these physical parameters, reservoir properties such as cementation factor and water saturation can be estimated by way of dielectric "mixing" laws (reflecting the effect of each component in the wave propagation). As the dielectric permittivity values of the matrix and the fluids are separately entered in the mixing law, they all should be accurately known in order to reliably estimate the reservoir properties. The simplest mixing law necessary for the interpretation of the complex permittivity measurements in oil reservoirs is a volumetric distribution of the effect on the complex wave number of the electromagnetic propagating wave; the law is called the CRIM law (reputed to be valid at frequencies around and greater than 1 MHz):

$$\sqrt{\in^*} = S_w \phi \sqrt{\in_w^*} + (1-S_w)\phi\sqrt{\in_{oi}} + (1-\phi)\sqrt{\in_{rk}}$$

Where:

$\in^* = \in + j\sigma/\omega\in_0$ Complex relative permittivity as measured by the tool;

$\in$ is the real part of the complex permittivity, generally called "dielectric constant" or relative permittivity;

$\sigma$ is the conductivity (S/m), $\omega=2\pi f$ the angular frequency of the signal, where f is the Hertzian frequency;

$\in_0$ the dielectric permittivity of vacuum;

$S_w$ Water saturation of offered volume, $(1-S_w)$ is the oil saturation;

$\phi$ Rock porosity (volume fraction of void volume);

$(1-\phi)$ is the rock matrix volume;

$\in_w^*$ the water complex permittivity depends on temperature and salinity, which can be inferred if the brine is known;

$\in_{oi}$ Oil dielectric constant (real, since oil conductivity is generally very low); and $\in_{rk}$ Matrix dielectric constant (real, since rock conductivity is generally very low).

Note that the matrix dielectric constant (real part of permittivity) can vary over a relatively large range (from 3 to 10 for instance). The water dielectric constant is in the range 50-100 and salinity can be assessed by various means, the conductivity of the medium being largely dependent on the conductivity of the water.

There is a need to obtain the relative dielectric constant of the rock (the real part of the permittivity) since it represents an offset in the measured data that has to be inferred by an independent means. A second input is the irreducible water saturation content of the cuttings.

The matrix dielectric constant from drilling cuttings from the same formation would provide this very important information for the dielectric measurement interpretation. Note that more complex mixture laws exist but all are based on the a priori knowledge of $\sqrt{\in_{rk}}$.

Various techniques for measurement of drilling cuttings have been discussed. For instance: Santarelli, Marsala, Brignoli, Rossi, N. Bona from AGIP in an SPE paper (36851), have reviewed advantages and disadvantages of formation evaluation based on measurements on cuttings. After drying the cuttings the porosity can be estimated by weighing the cuttings in a given volume and measure the air volume, and the sample mass.

In SPE/ISRM 47202 the same authors present a compact apparatus to measure low and very low permeability on cuttings in a cell with a pressure pulse excitation.

In an SPE paper (77563) a contingent method to measure permeability on cuttings is presented by IFP and IMFT ("Lenormand" school). The method is based on the injection of an oil into the cuttings placed in a chamber. When the oil enters the cuttings pores it expels Helium initially saturating the cuttings, the volume versus time of helium produced provides information on the cuttings permeability.

In an IADC/SPE 112687 paper "Automatic Measurement of Drilling Fluid and Drill Cuttings Properties", the authors present a complex set up measuring among various parameters density, pH, $H_2S$ content, liquid particle size distribution, mud solids or raman spectroscopy.

SUMMARY

According to some embodiments, a method of analyzing drilling cuttings is described. The method includes receiving drilling rock cuttings from subterranean rock formation, the rock cuttings being produced as part of a drilling process of a wellbore penetrating the rock formation; and analyzing the drilling rock cuttings so as to ascertain a measure of permittivity, such as complex permittivity and/or dielectric constant, associated with the rock cuttings.

According to some embodiments analyzing the drilling rock cuttings includes comparing the measure of permittivity to be ascertained with permittivity of known liquid mixtures. The rock cuttings can be saturated in a non-conductive fluid and one or more zero contrast measurements can be made.

According to some embodiments, the subterranean rock formation is part of a hydrocarbon reservoir, and the method is carried out in the vicinity of a wellsite, or at a location remote from the wellsite.

According to some embodiments, the subterranean rock formation is evaluated based on electromagnetic measurements and using the ascertained measure of permittivity.

According to some embodiments, a system for analyzing drilling rock cuttings is also described.

BRIEF DESCRIPTION OF THE FIGURES

The present disclosure is further described in the detailed description which follows, in reference to the noted plurality of drawings by way of non-limiting examples of exemplary embodiments, in which like reference numerals represent similar parts throughout the several views of the drawings, and wherein.

DETAILED DESCRIPTION

Figure 1:
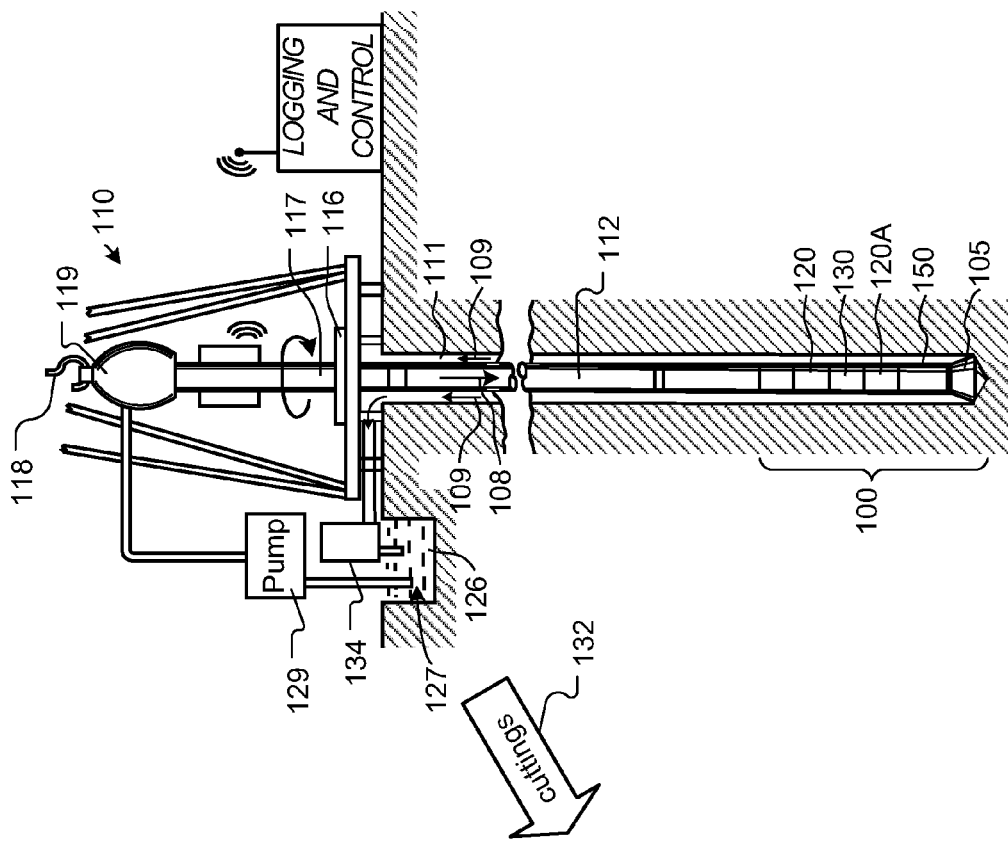
FIG. 1 illustrates an example of a wellbore drilling system and a cuttings analysis facility, according to some embodiments.
Figure 1:
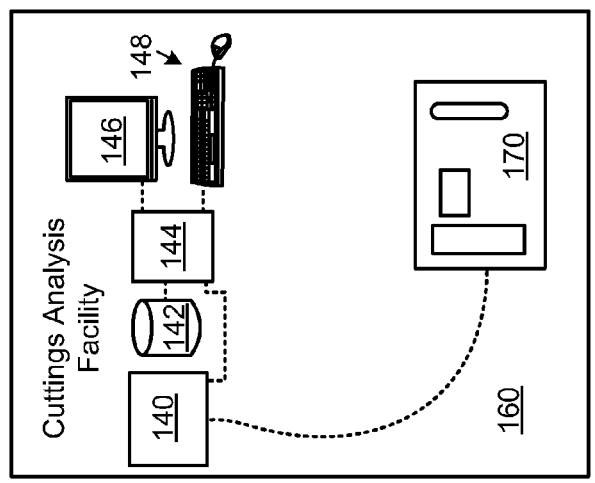

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicate like elements.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

According to some embodiments, the complex permittivity measured of rock cutting samples obtained during drilling operations and whose origin is known by flow rate analysis in the drilling system.

In terms of dielectric characteristics, the different parameters that can influence the mud cuttings are:

The complex permittivity of the reservoir brine $\in_b$;
The complex permittivity of the reservoir oil $\in_o$;
The complex permittivity of the reservoir gas $\in_g$;
The complex permittivity of the reservoir rock $\in_{rk}$;
The complex permittivity of the mud $\in_m$;
The cutting size distribution;
The cutting shape distribution;
The rock nature (lithology, composition);
Some contaminants and traces of various chemical elements; and
Temperature and pressure (for interface polarization).

During their journey from the drill bit to the surface the cuttings have been more or less saturated by the mud, the pressure has changed, the temperature has changed, dissolved gas may have formed bubbles, however the original irreducible water saturation would have been conserved, since no other effect than natural drainage imbibition would have acted to change this saturation (except for gas evolution).

According to some embodiments, various means can be used for rock cutting dielectric measurement in a cell. According to some preferred embodiments, the dielectric measurement is made by matching the unknown permittivity of the medium to be analyzed, to the permittivity of known liquid mixtures by successive saturation and looking for a "zero-contrast" measurement or any alternative methods of measurement on powders.

According to some other embodiments, the dielectric measurement is made by crushing, cleaning and drying the rock cuttings in powder, dispersing the powder in a fluid of low conductivity and known dielectric constant, weigh the fluid and the powder in a volume controlled chamber, measure the dielectric constant of the mixture and applying the CRIM law to extract the powder dielectric constant.

The use of the data is extremely important to complete the interpretation of dielectric analysis of the formation by the dielectric tool.

To be of value in this interpretation the origin of the cuttings (the geological layer where they come from) should be known. According to some embodiments, the average origin of cuttings can be obtained by flow-rate analysis of the mud in the drilling string.

FIG. 1 illustrates an example of a wellsite drilling system and a cuttings analysis facility in which the present invention can be employed, according to some embodiments. Note that the cuttings analysis facility 160 can be located at the wellsite (which can be onshore or offshore) or it can be located remotely from the wellsite.

In this exemplary system, a borehole 111 is formed in subsurface formations by rotary drilling in a manner that is well known. Embodiments of the invention can also use cuttings from directional drilling, as will be described hereinafter.

A drill string 112 is suspended within the borehole 111 and has a bottom hole assembly 100 which includes a drill bit 105 at its lower end. The surface system includes platform and derrick assembly 110 positioned over the borehole 111, the assembly 110 including a rotary table 116, Kelly 117, hook 118 and a rotary swivel 119. The drill string 112 is rotated by the rotary table 116, energized by means not shown, which engages the kelly 117 at the upper end of the drill string. The drill string 112 is suspended from a hook 118, attached to a traveling block (also not shown), through the kelly 117 and a rotary swivel 119 which permits rotation of the drill string relative to the hook. As is well known, a top drive system could alternatively be used.

In the example of this embodiment, the surface system further includes drilling fluid or mud 126 stored in a pit 127 formed at the well site. A pump 129 delivers the drilling fluid 126 to the interior of the drill string 112 via a port in the swivel 119, causing the drilling fluid to flow downwardly through the drill string 112 as indicated by the directional arrow 108. The drilling fluid exits the drill string 112 via ports in the drill bit 105, and then circulates upwardly through the annulus region between the outside of the drill string and the wall of the borehole, as indicated by the directional arrows 109. In this well known manner, the drilling fluid lubricates the drill bit 105 and carries formation cuttings up to the surface as it is returned to the pit 127 for recirculation. Before reaching the pit 127, the mud from the drillpipe passes through a cuttings collector 134 that is used to collect samples of cuttings from the drilling operation for analysis.

The bottom hole assembly 100 of the illustrated embodiment may comprise a logging-while-drilling (LWD) module 120, a measuring-while-drilling (MWD) module 130, a rotosteerable system and motor, and drill bit 105.

The LWD module 120 is housed in a special type of drill collar, as is known in the art, and can contain one or a plurality of known types of logging tools. It will also be understood that more than one LWD and/or MWD module can be employed, e.g. as represented at 120A. (References, throughout, to a module at the position of 120 can alternatively mean a module at the position of 120A as well.) The LWD module includes capabilities for measuring, processing, and storing information, as well as for communicating with the surface equipment. In the present embodiment, the LWD module includes a resistivity measuring device. According to some embodiments, the LWD module includes a directional resistivity measuring device.

The MWD module 130 is also housed in a special type of drill collar, as is known in the art, and can contain one or more devices for measuring characteristics of the drill string and drill bit. The MWD tool further includes an apparatus (not shown) for generating electrical power to the downhole system. This may typically include a mud turbine generator powered by the flow of the drilling fluid, it being understood that other power and/or battery systems may be employed. In the present embodiment, the MWD module includes one or more of the following types of measuring devices: a weight-on-bit measuring device, a torque measuring device, a vibration measuring device, a shock measuring device, a stick slip measuring device, a direction measuring device, and an inclination measuring device.

Figure 2:
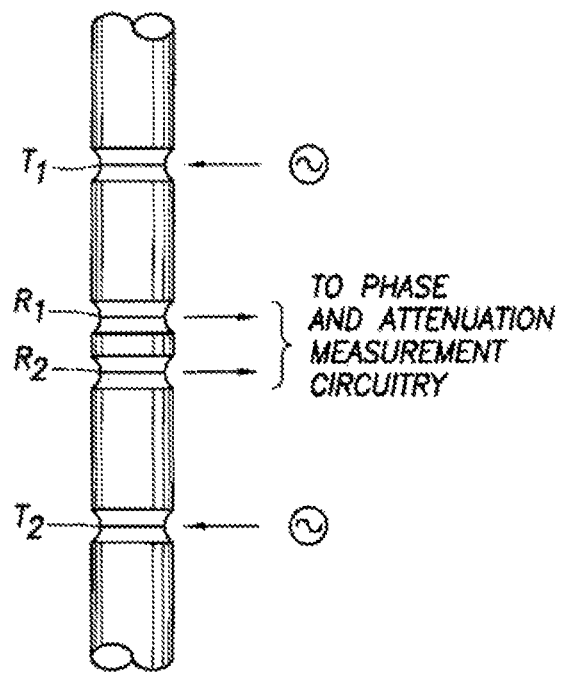
FIG. 2 depicts a resistivity logging-while-drilling tool, as part of the LWD tool or tools shown in FIG. 1, according to some embodiments.

An example of a tool which can be the LWD tool 120, or can be a part of an LWD tool suite 120A of the system and method hereof, is the dual resistivity LWD tool disclosed in U.S. Pat. No. 4,899,112 and entitled "Well Logging Apparatus And Method For Determining Formation Resistivity At A Shallow And A Deep Depth," incorporated herein by reference. As seen in FIG. 2, upper and lower transmitting antennas, $T_1$ and $T_2$, have upper and lower receiving antennas, $R_1$ and $R_2$, therebetween. The antennas are formed in recesses in a modified drill collar and mounted in insulating material. The phase shift of electromagnetic energy as between the receivers provides an indication of formation resistivity at a relatively shallow depth of investigation, and the attenuation of electromagnetic energy as between the receivers provides an indication of formation resistivity at a relatively deep depth of investigation. The above-referenced U.S. Pat. No. 4,899, 112 can be referred to for further details. In operation, attenuation-representative signals and phase-representative signals are coupled to a processor, an output of which is coupleable to a telemetry circuit.

Figure 3:
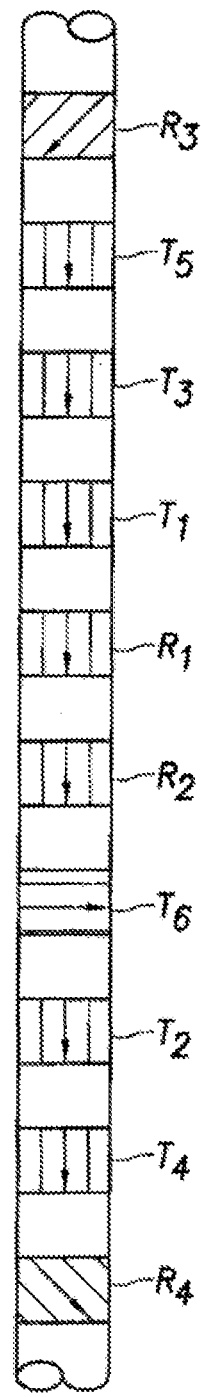
FIG. 3 depicts a directional deep-reading logging-while-drilling drilling tool, as part of the LWD tool or tools 120 in FIG. 1, according to some other embodiments.

FIG. 3 depicts a directional deep-reading logging-while-drilling drilling tool, as part of the LWD tool or tools 120 in FIG. 1, according to another embodiment. Signals from tools having axially aligned cylindrically symmetrical coils are not directionally sensitive. The tool of FIG. 3 provides tilted and transverse coils to obtain directionally sensitive measurements. The sensor array includes six transmitter antennas and four receiver antennas. Five transmitter antennas ($T_1$ through $T_5$) are arranged axially along the length of the tool. A sixth transmitter antennas ($T_6$) is oriented transverse to the tool axis. A receiver antenna is positioned at each end of the tool. This pair of receiver antennas ($R_3$ and $R_4$) brackets the transmitters, and each of these receivers is tilted 45 degrees to the tool axis. An additional pair of receiver antennas ($R_1$ and $R_2$), located in the center of the transmitter array, is arranged axially and can obtain conventional type propagation resistivity measurements. The described arrangement produces a preferential sensitivity to conductivity on one side of the tool. As the tool rotates, its sensors can detect nearby conductive zones and register the direction from which maximum conductivity can be measured. Magnetometers and accelerometers can provide reference directional orientation data for the tool. In addition to its directional capability, the tool provides relatively deeper measurements than most conventional LWD resistivity tools. The substantially real time bidirectional drill string telemetry hereof, in conjunction with the capabilities of the directional resistivity logging tool, as described, improves performance of geosteering by increasing the amount of data at the surface and the speed and precision of directional drilling control.

Referring again to FIG. 1, cuttings 132 are collected from cuttings collector 134 and are transported to the cuttings analysis facility 160. Facility 160 includes one or more central processing units 140, storage system 144, communications and input/output modules 140, a user display 146 and a user input system 148. Input/output modules 140 include modules to communicate with and control cuttings analysis instruments 170.

Figure 4:
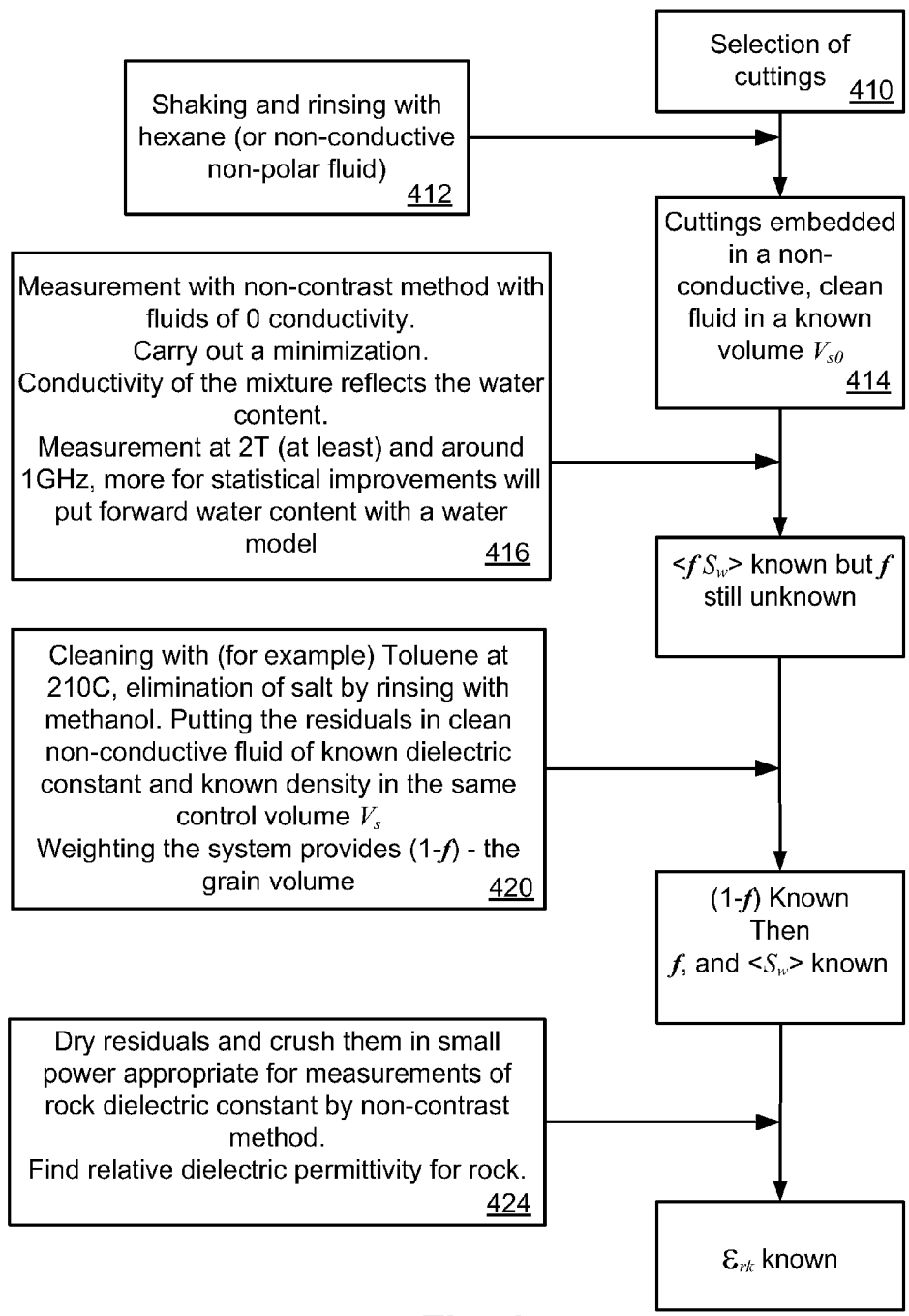
FIG. 4 illustrates steps in analyzing drillings cuttings for determining permittivity, according to some preferred embodiments.

FIG. 4 illustrates steps in analyzing drillings cuttings for determining permittivity, according to some embodiments. In step 410 of the cuttings analysis process, a given amount of mud cutting taken in a given sample of volume $V_s$ selected in the incoming cuttings, such as from the cuttings collector 134 shown in FIG. 1. In step 412, the mixture is filtered, shaken and rinsed with an alkane, hexane for instance (i.e. with low dielectric constant and no electric conductivity) with the aim to eliminate the mud. What does remain in $V_s$ is a series of porous cuttings holding some mud filtrate, irreducible oil (or) gas saturation and irreducible water saturation, and surrounded by the alkane.

Assuming that the cuttings are of the same nature and same porosity, in steps 414 and 416, the cuttings are then immersed in non-conductive fluids of known dielectric permittivity which will vary from high to low value in such a way that the mixture will have a minimal non-contrast with the mixture value. The real part of the permittivity of the medium should then coincide with the non-conductive permittivity of the mixture, but the conductivity of the medium should then be in proportion with the irreducible water content of the cuttings. In order to know the porosity of the mixture, the density of each fluid and later the density of the rock powder are preferably carefully determined and recorded. According to some embodiments, the irreducible water saturation is obtained by carrying out measurements at different temperatures of the dielectric permittivity. The water content is extracted knowing the water salinity (through a "water model" which can be very accurate).

In step 420, the mixture is then cleaned with toluene at 210C and with methanol to eliminate the residuals of salts. In step 424 the mixture is dried at high temperature in the same cell. The residuals will be again tested with the non-contrast method to get the exact dielectric constant of the rock. According to some embodiments, the rock permittivity is stored for a dielectric survey with wireline tools or as a dielectric survey on cores.

Note that $V_s$ contains several components. According to some embodiments, the dielectric measurement of the mixture can be examined initially (indexed by the subscript 0) at different frequencies.

The surface polarization of some components like asphaltene solutions can also depend on temperature inducing specific dielectric response (See e.g. Colloids & Surfaces A 106 (1996) 33-47; Syunyaev & Likhatsky, Energy Fuels 2010). Typical signature of this phenomenon is in the range around $10^4$ to $10^5$ Hertz. Since mixtures of various components may have interfered with the oil content in the cuttings, the focus is put on the residual water content of the cuttings. The CRIM law is reputed to express the volumetric dependence of the travelling wave number versus the amount of each component at frequencies (typically around and greater than 1 GHz).

If information can be extracted in residual saturation by surface polarization exploration of the frequency dispersion curves in the lower range can be achieved.

$V_{s0}$ contains a series of elements: the rock cuttings, imbibed with oil, gas, brine and mud filtrate, and any component not diffused during the travel of the sample from the drilling bit to the surface.

For the sake of recording dielectric data $\in(V_{s0})$ will be recorded and the value will be stored.

$V_{s0}$ contains rock debris and non-conductive fluids (oil, gas), fluids with temperature variable dielectric constant (essentially water). $\in(V_{s0},T)$ will thus be recorded at different temperatures in a confined chamber where the pressure can be controlled. Since only the water will vary in this circumstance we use the CRIM law to determine the water content of the mixture. By neglecting the variation of volume due to temperature, and knowing that the permittivity of all other components than water do not depend on temperature, the amount of water in the sample can be deduced by the measurement at 2 temperatures and at frequencies around 1 GHz, $\sqrt{\in^*(T_1)}$ and $\sqrt{\in^*(T_2)}$ then:

$$\sqrt{\varepsilon^*(T_1)} = S_w\phi\sqrt{\varepsilon_w^*(T_1)} + (1-S_w-S_{md})\phi\sqrt{\varepsilon_{oi}} + S_{md}\phi\sqrt{\varepsilon_{md}} + (1-\phi)\sqrt{\varepsilon_{rk}} \quad (1)$$

$$\sqrt{\varepsilon^*(T_2)} = S_w\phi\sqrt{\varepsilon_w^*(T_2)} + (1-S_w-S_{md})\phi\sqrt{\varepsilon_{oi}} + S_{md}\phi\sqrt{\varepsilon_{md}} + (1-\phi)\sqrt{\varepsilon_{rk}} \quad (2)$$

$$\ldots$$

$$\sqrt{\varepsilon^*(T_i)} = S_w\phi\sqrt{\varepsilon_w^*(T_i)} + (1-S_w-S_{md})\phi\sqrt{\varepsilon_{oi}} + S_{md}\phi\sqrt{\varepsilon_{md}} + (1-\phi)\sqrt{\varepsilon_{rk}} \quad (3)$$

In order to improve the accuracy of the process, multiple temperatures can be used leading to a statistical average of $S_w\phi$.

$$\frac{1}{N^*}\sum_{i>j=1}^{N} \frac{\sqrt{\varepsilon^*(T_i)} - \sqrt{\varepsilon^*(T_j)}}{\sqrt{\varepsilon_w^*(T_i)} - \sqrt{\varepsilon_w^*(T_j)}} = <S_w\phi> \quad (4)$$

where $N^* = \dfrac{N(N-1)}{2}$ for $N$ even and $N^* = \dfrac{N^2}{2}$ for $N$ odd.

This requires knowledge of the porosity of the mixture. According to some embodiments, this will be found only at the last stage of the process when the cuttings will be dried, cleaned, crushed and remixed with a known quantity of fluid in a given volume, leading to the knowledge of $(1-\phi)$ and therefore of $<S_w\phi>$ by elimination of $\phi$.

This closes the loop of the set of measurements used to obtain the desired parameters, according to some preferred embodiments.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the invention should not be viewed as limited except by the scope and spirit of the appended claims.

What is claimed is:

1. A method of analyzing drilling cuttings comprising:
    receiving drilling rock cuttings from subterranean rock formation, the rock cuttings being produced as part of a drilling process of a wellbore penetrating the rock formation; and
    analyzing, at least in part using a processing system, the drilling rock cuttings so as to ascertain a measure of permittivity associated with the rock cuttings wherein the analyzing of the drilling rock cuttings includes saturating the rock cuttings in a non-conductive fluid.

2. A method according to claim 1 wherein the measure of permittivity is complex permittivity.

3. A method according to claim 1 wherein the measure of permittivity is a measure of a dielectric constant associated with the rock cuttings.

4. A method according to claim 1 wherein the analyzing the drilling rock cuttings includes comparing the measure of permittivity to be ascertained with permittivity of known liquid mixtures.

5. A method according to claim 1 wherein the analyzing of the cuttings includes one or more zero contrast measurements.

6. A method according to claim 1 wherein the analyzing of the cuttings includes crushing the cuttings into a cuttings powder, cleaning and drying the cuttings powder, dispersing the cuttings powder in a fluid to form a mixture, weighing the mixture, and measuring a dielectric constant of the mixture.

7. A method according to claim 1 wherein the subterranean rock formation is part of a hydrocarbon reservoir.

8. A method according to claim 1 wherein the method is carried out in the vicinity of a wellsite associated with the wellbore.

9. A method according to claim 1 wherein the method is carried out in a facility located remotely from the wellbore.

10. A method according to claim 1 further comprising evaluating at least portions of the subterranean rock formation based on electromagnetic measurements and the ascertained measure of permittivity.

11. A system for analyzing drilling rock cuttings comprising:

one or more instruments adapted to ascertain a measure of permittivity associated with drilling rock cuttings produced as part of a drilling process of a wellbore penetrating a subterranean rock formation; and a processing system adapted and programmed to aid in ascertaining the measure of permittivity and storing values relating to the ascertained measure of permittivity wherein the analyzing of the drilling rock cuttings includes saturating the rock cuttings in a non-conductive fluid.

12. A system according to claim 11 wherein the measure of permittivity is complex permittivity.

13. A system according to claim 11 wherein the measure of permittivity is a measure of a dielectric constant associated with the rock cuttings.

14. A system according to claim 11 wherein the one or more instruments are adapted to compare the measure of permittivity to be ascertained with permittivity of known liquid mixtures.

15. A system according to claim 11 wherein the subterranean rock formation is part of a hydrocarbon reservoir.

16. A system according to claim 11 further comprising a cuttings collector adapted to collect cuttings from the subterranean rock formation during the drilling process.

17. A system according to claim 11 further comprising a second processing system adapted and programmed to evaluate the subterranean rock formation based on electromagnetic measurements and the stored values relating to the ascertained measure of permittivity.

\* \* \* \* \*